US008643840B2

(12) United States Patent
Gross et al.

(10) Patent No.: US 8,643,840 B2
(45) Date of Patent: Feb. 4, 2014

(54) CELL FOR LIGHT SOURCE

(75) Inventors: Kenneth P. Gross, San Carlos, CA (US);
Yung-Ho Chuang, Cupertino, CA (US);
John Fielden, Los Altos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 228 days.

(21) Appl. No.: 13/119,571

(22) PCT Filed: Feb. 17, 2011

(86) PCT No.: PCT/US2011/025198
§ 371 (c)(1),
(2), (4) Date: Mar. 17, 2011

(87) PCT Pub. No.: WO2011/106227
PCT Pub. Date: Sep. 1, 2011

(65) Prior Publication Data
US 2011/0205529 A1    Aug. 25, 2011

Related U.S. Application Data

(60) Provisional application No. 61/308,206, filed on Feb. 25, 2010.

(51) Int. Cl.
*G01N 21/73*    (2006.01)
*H01S 3/225*    (2006.01)

(52) U.S. Cl.
USPC .............................. 356/327; 356/316; 372/76

(58) Field of Classification Search
USPC .............. 250/504 R, 426; 356/322, 327, 326, 356/369, 364, 630, 614, 337–343, 600, 60, 356/612
See application file for complete search history.

(56) References Cited

U.S. PATENT DOCUMENTS

| | | | |
|---|---|---|---|
| 4,043,308 A * | 8/1977 | Cerkanowicz | 123/143 R |
| 4,063,803 A * | 12/1977 | Wright et al. | 359/894 |
| 5,424,608 A * | 6/1995 | Juengst et al. | 313/623 |
| 5,747,813 A | 5/1998 | Norton et al. | |
| 6,970,492 B2 * | 11/2005 | Govorkov et al. | 372/55 |
| 7,202,951 B1 | 4/2007 | Janik et al. | |
| 2002/0101900 A1 * | 8/2002 | Govorkov et al. | 372/57 |
| 2004/0036393 A1 * | 2/2004 | Eastlund et al. | 313/26 |
| 2007/0228288 A1 * | 10/2007 | Smith | 250/426 |
| 2008/0087847 A1 | 4/2008 | Bykanov et al. | |

* cited by examiner

*Primary Examiner* — Gregory J Toatley
*Assistant Examiner* — Maurice Smith
(74) *Attorney, Agent, or Firm* — Luedeka Neely Group, P.C.; Rick Barnes

(57) ABSTRACT

A cell for a vacuum ultraviolet plasma light source, the cell having a closed sapphire tube containing at least one noble gas. Such a cell does not have a metal housing, metal-to-metal seals, or any other metal flanges or components, except for the electrodes (in some embodiments). In this manner, the cell is kept to a relatively small size, and exhibits a more uniform heating of the gas and cell than can be readily achieved with a hybridized metal/window cell design. These designs generally result in higher plasma temperatures (a brighter light source), shorter wavelength output, and lower optical noise due to fewer gas convection currents created between the hotter plasma regions and surrounding colder gases. These cells provide a greater amount of output with wavelengths in the vacuum ultraviolet range than do quartz or fused silica cells. These cells also produce continuous spectral emission well into the infrared range, making them a broadband light source.

10 Claims, 5 Drawing Sheets

CELL FOR LIGHT SOURCE

This application claims all rights and priority on U.S. provisional patent application Ser. No. 61/308,206 filed 2010 Feb. 25 and PCT patent application serial number US2011/025198 filed 2011 Feb. 17. This invention relates to the field of integrated circuit fabrication. More particularly, this invention relates to plasma light sources that emit broadband radiation including the vacuum ultraviolet range.

FIELD

Introduction

Plasma discharge is used as a light source in a variety of different applications, such as in the inspection and metrology of integrated circuits. The most common commercially available vacuum ultraviolet (VUV) light source is a low pressure deuterium discharge lamp, which exhibits a relatively high radiant output at wavelengths from about 120 nanometers to about 160 nanometers, but a relatively low radiant output at wavelengths greater than about 170 nanometers. Since for many applications it is desirable to use broadband radiation that spans vacuum ultraviolet, ultraviolet, visible and near infrared ranges, for those applications it is currently necessary to combine the output of a deuterium lamp with the output from another lamp such as a xenon arc lamp or quartz-halogen lamp to cover the whole wavelength range.

A hot, high-pressure xenon plasma can emit radiation covering the vacuum ultraviolet through near infrared wavelength ranges. However conventional xenon arc lamps are enclosed in fused silica envelopes. Hot fused silica does not transmit wavelength shorter than about 180 nanometers, so there is little useful output from the light source in the vacuum ultraviolet part of the spectrum.

Commercially available vacuum ultraviolet deuterium lamps overcome the problem of the poor vacuum ultraviolet transmission of fused silica by using a small magnesium fluoride output window that is fused or bonded onto the end of a snout in the fused silica envelope. Magnesium fluoride transmits light from about 115 nanometers to about 8 microns in wavelength. Bonding between the magnesium fluoride window and fused silica is mechanically weak. A deuterium lamp operates at low pressure, so the force on the window is a compressive force from the outside due to atmospheric pressure. If the deuterium lamp is operated in a vacuum, then the force on the window is a weak outward force due to the low pressure gas in the lamp. In either case the pressure difference between inside and outside of the envelope will not exceed one atmosphere. The force on the window of a deuterium lamp is always low enough that a properly formed bond between the window and envelope does not fail.

In order to obtain high brightness emission from a xenon plasma over a broad range of wavelengths, it is necessary that the xenon be at high pressure, typically about ten to thirty atmospheres. Such a high pressure precludes the use of a magnesium fluoride window in the fused silica envelope because the bond between the window and the envelope cannot reliably withstand the outward forces caused by the high pressure difference between inside and outside the envelope.

What is needed, therefore, is a light source that reduces problems such as those described above, at least in part, while providing high brightness radiation over a broad spectral range including vacuum ultraviolet, ultraviolet and visible wavelengths.

SUMMARY OF THE CLAIMS

The above and other needs are met by a cell for a vacuum ultraviolet plasma light source, the cell having a closed sapphire tube containing at least one noble gas.

Such a cell does not have a metal housing, metal-to-metal seals, or any other metal flanges or components, except for the electrodes (in some embodiments). In this manner, the cell is kept to a relatively small size, and exhibits a more uniform heating of the gas and cell than can be readily achieved with a hybridized metal/window cell design. These designs generally result in higher plasma temperatures (a brighter light source), shorter wavelength output, and lower optical noise due to fewer gas convection currents created between the hotter plasma regions and surrounding colder gases. These cells provide a greater amount of output with wavelengths in the vacuum ultraviolet range than do quartz or fused silica cells. These cells also produce continuous spectral emission well into the infrared range, making them a broadband light source.

In various embodiments according to this aspect of the invention, the cell is formed exclusively of sapphire or other VUV-transmissive material. In some embodiments the at least one noble gas includes a mixture of xenon with at least one of argon, krypton, neon and helium. In some embodiments mercury is added to the at least one noble gas. In some embodiments electrodes extend through the tube into the cell, where the electrodes are hard-sealed to the sapphire of the tube. In some embodiments the sapphire tube is closed by means of two end caps that are diffusion bonded to the tube. In some embodiments at least one of the end caps is formed of a more pure grade of sapphire than the tube. In some embodiments one of the end caps is coated with an anti-reflective coating so that a laser light directed into the cell through the coated end cap exhibits a reduced degree of reflectance.

In some embodiments, the light, instead of entering and/or leaving via the end caps, enters and/or leaves through the sidewalls of the tube. In some embodiments the sapphire tube has a flat window formed therein, wherein the flat window is formed of a more pure grade of sapphire than the tube. In some embodiments one region of the surface of the cylinder is coated with an anti-reflective coating. In other embodiments a different region of the surface of the cylinder is coated with a reflective coating. In some embodiments, an anti-reflective coating is coated on the outside of a flat window.

According to another aspect of the invention there is described a vacuum ultraviolet plasma light source having a cell having a closed sapphire tube containing at least one noble gas, means for initiating a plasma within the cell, and means for sustaining a plasma within the cell, thereby creating a vacuum ultraviolet light.

In various embodiments according to this aspect of the invention, the means for initiating the plasma within the cell includes at least one of a direct current potential applied by electrodes extending into the cell, an alternating current potential applied by electrodes extending into the cell, a pulsed laser directed into the cell, a continuous laser directed into the cell, microwaves directed into the cell, radio frequency electromagnetic radiation directed into the cell, ionizing radiation of gamma rays directed into the cell, ionizing radiation of X-rays directed into the cell, ionizing radiation of alpha particles directed into the cell, and ionizing radiation of beta particles directed into the cell.

In some embodiments the means for sustaining a plasma within the cell includes at least one of a direct current potential applied by electrodes extending into the cell, an alternating current potential applied by electrodes extending into the cell, a pulsed laser directed into the cell, and a continuous laser directed into the cell. Some embodiments include an aperture formed in a light-stop, where the aperture passes only a desired portion of the vacuum ultraviolet light. In some embodiments the means for sustaining the plasma comprises a laser light source coupled to a fiber optic for directing a laser beam into the cell.

According to yet another aspect of the invention there is described a spectrographic instrument having a selection of the components described above.

BRIEF DESCRIPTION OF THE DRAWINGS

Further advantages of the invention are apparent by reference to the detailed description when considered in conjunction with the Figures, which are not to scale so as to more clearly show the details, wherein like reference numbers indicate like elements throughout the several views, and wherein.

DETAILED DESCRIPTION

One aspect of some embodiments of the present invention is a sealed plasma discharge cell formed entirely of glass that can contain pressures of up to about fifty atmospheres of an appropriate gas, such as helium, neon, argon, krypton, and xenon. The term "glass" as used herein has a specific definition, which is that the material is optically transmissive within the desired wavelength range. However, it does not denote that the material is necessarily formed of silica, or that the material is amorphous. In most embodiments, the material from which the cell is formed is in a crystalline state.

Figure 1:
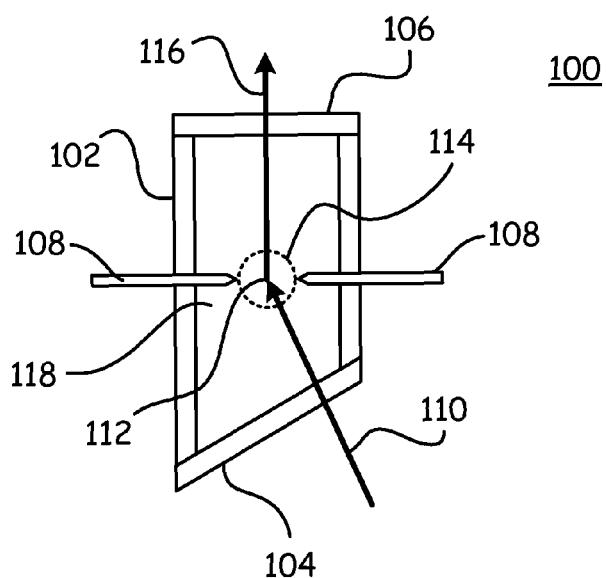
FIG. 1 is a cross-sectional view of a light source according to a first embodiment of the present invention.

With reference now to FIG. 1 there is depicted a schematic illustration of one embodiment of a bonded sapphire plasma discharge cell 100. The cell 100 has sidewalls 102, such as formed of a cylinder of sapphire with a diameter of less than about two centimeters. An end-plate 104 is disposed at one end of the cell wall 102, and is diffusion bonded to the cell wall 102. An end-plate 106 is disposed at the other end of the cell wall 102, and is also diffusion bonded to the cell wall 102. In some embodiments the end-plates 104 and 106 are also formed of sapphire, and in other embodiments they are formed of other materials. In some embodiments, the entire volume of the cell 100 is about two cubic centimeters.

The cell 100 is filled with a gas 118. In one embodiment the gas 118 is xenon at an initial room-temperature-pressure of between about two and about fifty atmospheres. In other embodiments, other noble gases or mixtures of noble gases at such pressures are used. In some embodiments, mixtures of xenon and argon, xenon and krypton, and xenon and neon are used. Trace amounts of other elements such as mercury are added in some embodiments to more efficiently excite the atomic energy levels of interest.

Electrodes 108 are positioned to either provide a direct current potential to a central spot 112 within the cell 100, so as to sustain a plasma discharge 114 within the cell 100, or to "start" or ionize the plasma 114 when using an alternate energy source such as a laser beam 110, or application of radio frequency energy. Regardless of how it is initiated or sustained, the plasma 114 produces an output light 116 having the properties as desired and described herein. The electrodes 108 are sealed to the side walls 102 of the cell 100 such as with a hard-sealing technique.

Figure 2:
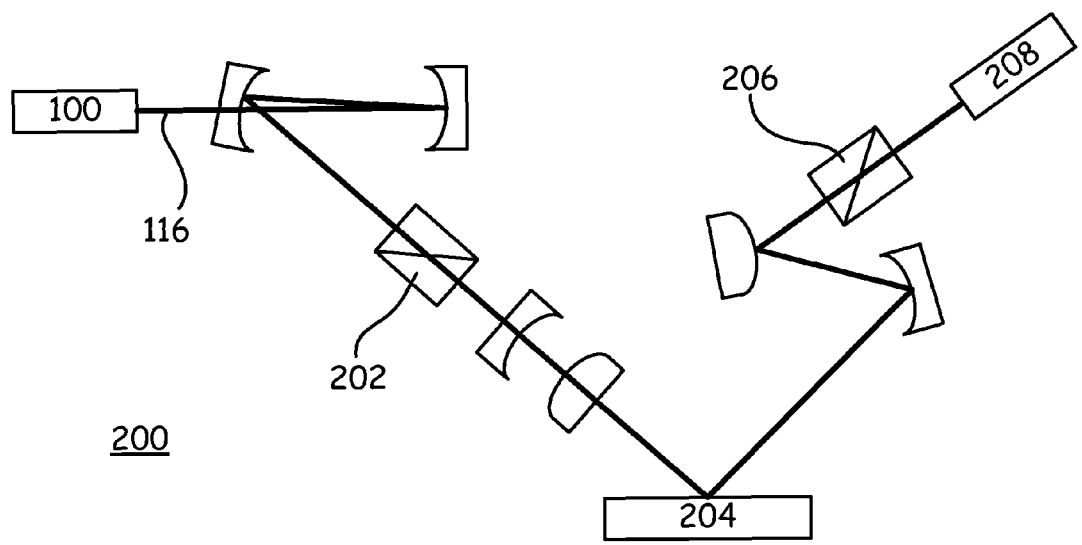
FIG. 2 is a functional block diagram of a broadband spectroscopic ellipsometer according to a first embodiment of the present invention.

FIG. 2 depicts an ellipsometer 200 that uses the broadband light source cell 100 described above. The output beam 116 is passed through a variety of optics, including in some embodiments a polarizer 202, and is reflected off of a substrate 204. In some embodiments the beam 116 passes through an analyzer 206, before being received by a spectrograph 208. More details of an ellipsometer that can use this broadband light source can be found in U.S. Pat. No. 6,734,967. It should be understood that the ellipsometer optics shown in FIG. 2 do not all lie in one plane. Some of the optical elements lie above or below the plane of the page and are shown in projection with the light passing in front of, or behind, those elements.

Figure 3:
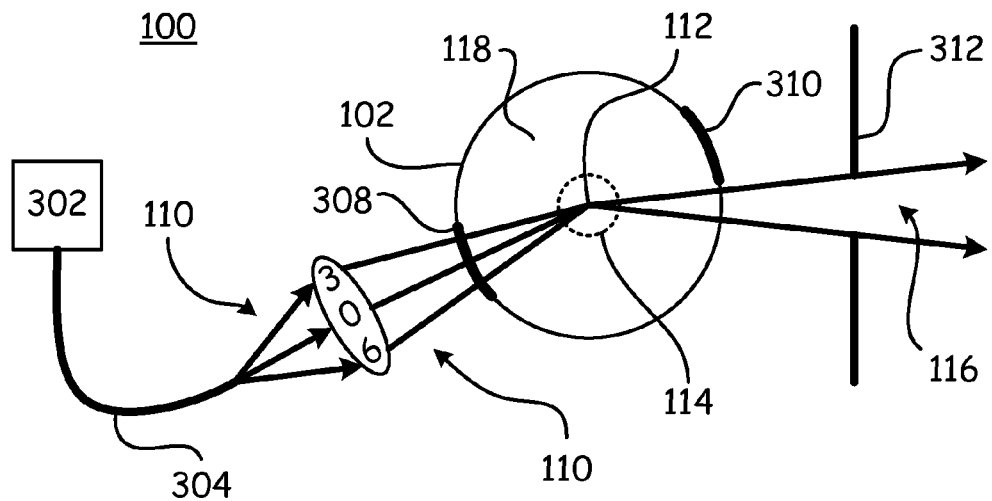
FIG. 3 is a cross sectional view of a light source according to a second embodiment of the present invention.
Figure 4:
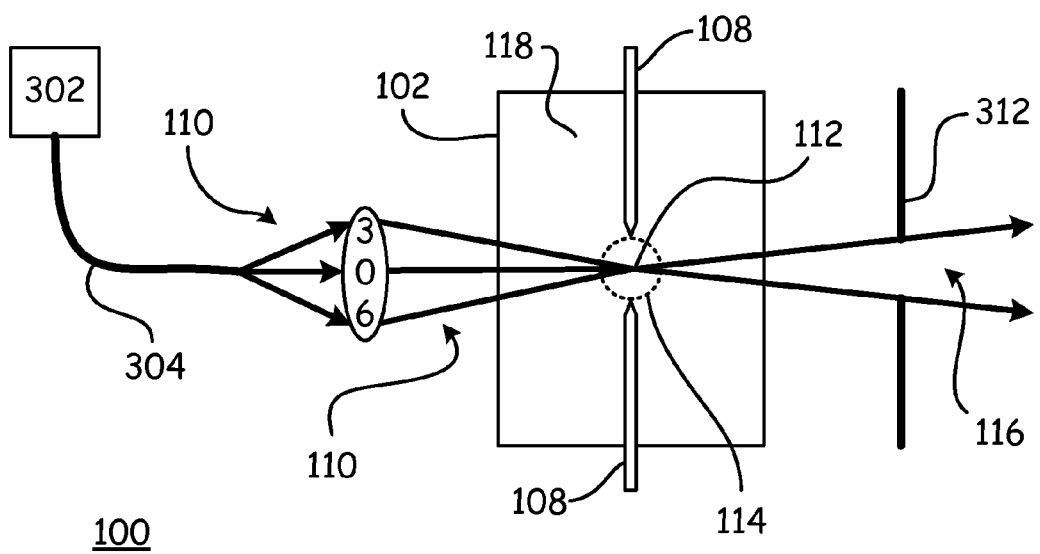
FIG. 4 is a top plan view of a light source according to the second embodiment of the present invention.

FIG. 3 is a cross-sectional view of another embodiment of the present invention. FIG. 4 is a top plan view of the same embodiment. In this embodiment the sealed cylinder 102 is formed of sapphire or some other material that is transmissive to vacuum ultraviolet wavelengths to at least some extent. The cylinder 102 has a diameter of about one centimeter, though larger and smaller diameters would also be acceptable. The length of the cylinder 102 is between about one centimeter and about ten centimeters, though longer and shorter lengths would also be acceptable.

In some embodiments, laser light 110 is delivered by a fiber optic 304 from a laser source 302. Light 110 emitted from the end of the fiber optic 304 is focused by a lens 306 to a point 112 near the center of the cylinder 102 to maintain a hot plasma 114 in the gas 118. In some embodiments the wavelength of the laser light 110 is in the infrared range, such that it is only weakly absorbed by the gas atmosphere 118, but is strongly absorbed by the hot plasma 114. For xenon gas, wavelengths of between about 970 nanometers and about 975 nanometers are used in one embodiment. Wavelengths of about 515 nanometers, about 523 nanometers, about 527 nanometers, or about 532 nanometers are used in other embodiments. In one embodiment, the power of the laser 302 is in the range of from about twenty watts to about two-hundred and fifty watts. In one embodiment, the power of the laser 302 is between about fifty watts and about sixty watts. In one embodiment, the laser 302 consists of at least one diode laser coupled to the same fiber optic 304. In another embodiment a fiber laser 302 is used. In another embodiment a gas laser 302 is used. In another embodiment a diode-pumped solid-state laser 302 is used.

The lens 306 can be implemented in many different ways. It some embodiments the lens 306 is a singlet, doublet, or triplet lens. In some embodiments it is comprised of one or more curved mirrors. In some embodiments it is a combination of minors and lenses. In some embodiments, flat minors are used to change the direction of the light to allow the fiber optic 304 to be conveniently located. Any or all of the mirrors or lenses directing the laser beam 110 in different embodiments have coatings to optimize the transmission of the laser wavelength from the fiber optic 304 to the plasma 114. When minors are used, one or more minors can be coated to maximize the reflection of the wavelength of the laser light 110. When lenses are used, one or more lens surfaces can be coated with anti-reflection coatings to maximize the transmission of the laser light 110.

The plasma 114 emits broad-band radiation 116 spanning wavelengths from the vacuum ultraviolet to the near infrared, in all directions. For example, the wavelengths emitted may include a range of from about 155 nanometers to about one thousand nanometers. Some of the emitted light 116 passes through an output port 312. The light 116 passing though the output port 312 can be used in a metrology instrument, such as the ellipsometer 200 depicted in FIG. 2. The light 116 can also be used in a reflectometer. U.S. Pat. No. 5,747,813 describes a small-spot broad-band spectroscopic reflectometer that might advantageously use the light source described herein. The light 306 can also be used in an inspection system that detects reflected or scattered light.

In some embodiments, two electrodes 108 are installed along the length of the cell 102, with a gap disposed between them, near the point 112 where the laser light 110 is focused. The gap in some embodiments is between about one millimeter and five millimeters in length, though shorter and longer gaps can also be made to work. Gas-tight seals are formed between the electrodes 108 and the material of the cell 102. The electrodes 108 in some embodiments are either brazed or soldered to the material of the cell 201. An electrical discharge (such as a spark or arc) is used in some embodiments to create an initial plasma that absorbs the laser light 110 more efficiently than the neutral gas 118. A brief pulse of a voltage between about one kilovolt and fifty kilovolts is used in some embodiments to create a short-lived electrical discharge. Once the plasma 114 starts absorbing the laser light 110, the plasma 114 becomes self-sustaining and the discharge is no longer needed. The electrical discharge in some embodiments is a series of pulses repeated every few milliseconds until a self-sustaining plasma 114 is created. The electrical discharge can be either direct current or alternating current. The repetition rate of the pulses in some embodiments is between about one megahertz and one hertz, though lower or higher rates may be used.

Alternate embodiments of the light source 100 disclosed herein do not use an electrical discharge to create the initial plasma 114, but instead use a pulsed laser, microwaves, radio frequency electromagnetic radiation, or ionizing radiation such as gamma rays, X-rays, alpha particles, or beta particles. In various embodiments, such a source of ionizing radiation is disposed either within the gas mixture 118, or outside the cell 102.

Figure 6:
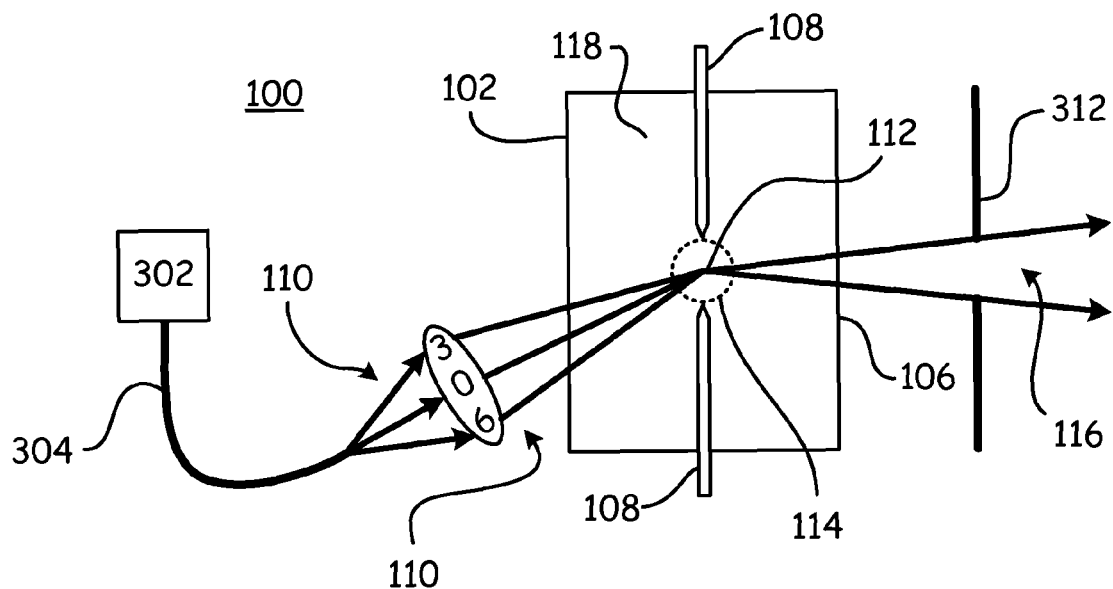
FIG. 6 is a top plan view of a light source according to the third embodiment of the present invention.

In one embodiment, the cylinder 102 lies approximately horizontally. In one embodiment, the laser light 110 is focused from below the horizontal, as illustrated in FIG. 3. In one embodiment, the laser light 110 is aimed from about thirty degrees below the horizontal. In another embodiment, the laser light 110 is focused from above the horizontal, such as about thirty degrees above the horizontal. In another embodiment, the laser light 110 comes from near the horizontal. In one embodiment the laser light 110 is directed from one side as illustrated in FIG. 6 in top-plan view. In any of these embodiments the relative angle between the laser light 110 and the output port 312 may be chosen so as to avoid the laser light 110 being directly transmitted through the output port 312.

Figure 8:
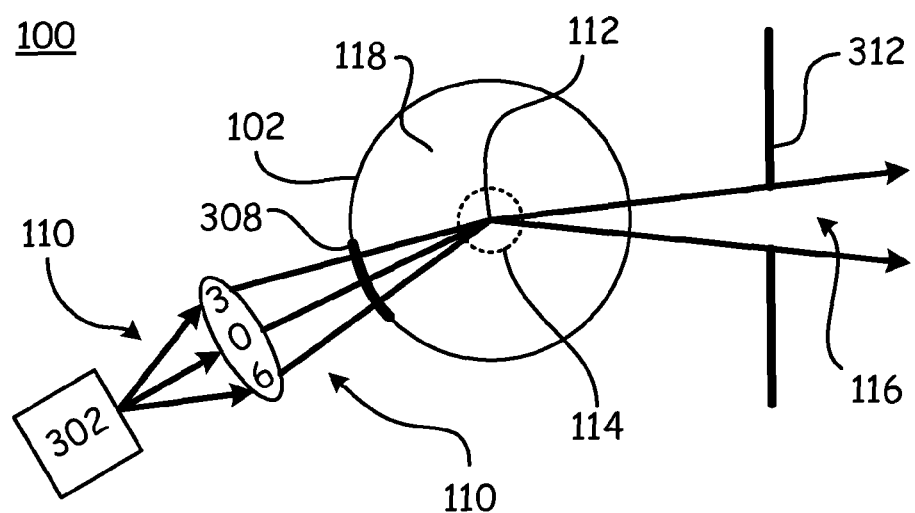
FIG. 8 is a cross-sectional view of a light source according to a fourth embodiment of the present invention.

In some embodiments, the cylinder 102 has an anti-reflection coating 308, as depicted in FIGS. 3 and 8. The coating 308 is selectively coated on part of the surface of the cylinder 102 to enhance the transmission of the laser light 110 through the material. Since such a coating 308 is likely to not be transmissive at vacuum ultraviolet wavelengths, in some embodiments the coating 308 is omitted from the region of the cylinder 102 through which the emitted light 116 passes.

Figure 7:
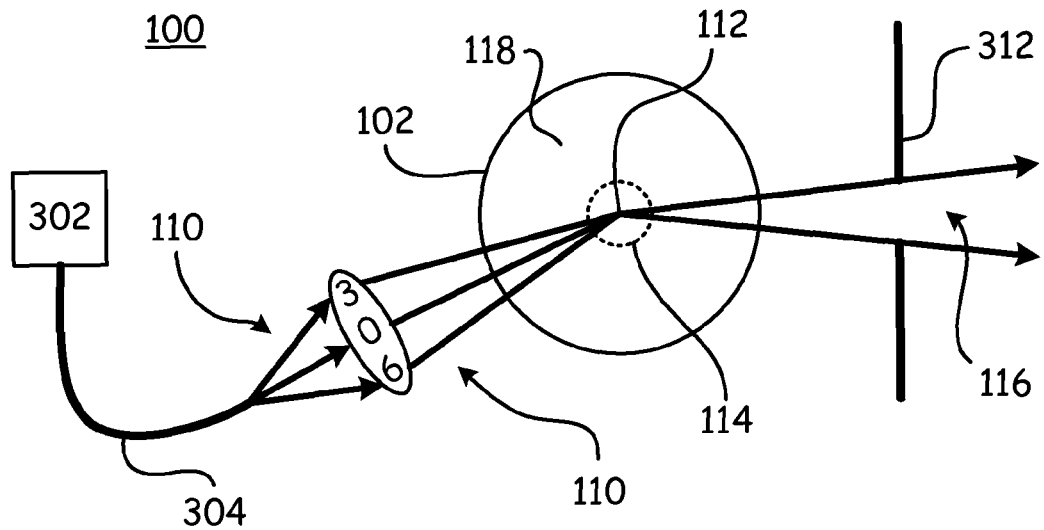
FIG. 7 is a cross-sectional view of a light source according to a fourth embodiment of the present invention.

In some embodiments as depicted in FIG. 3, the cylinder 102 has a coating 310 designed to reflect the laser light 110 that passes through the plasma 114, back into the gas 118. Since such a coating 310 is likely to not be transmissive at vacuum ultraviolet wavelengths, in some embodiments the coating 310 is omitted from the region of the cylinder 102 through which the emitted light 116 passes. FIG. 7 depicts the cell 102 without the coatings 308 and 310.

Although the cell 102 is depicted as a cylinder, other shapes for the cell 102 are also contemplated herein. For example, in various embodiments the cell 102 is a sphere or an oblate spheroid.

Figure 5:
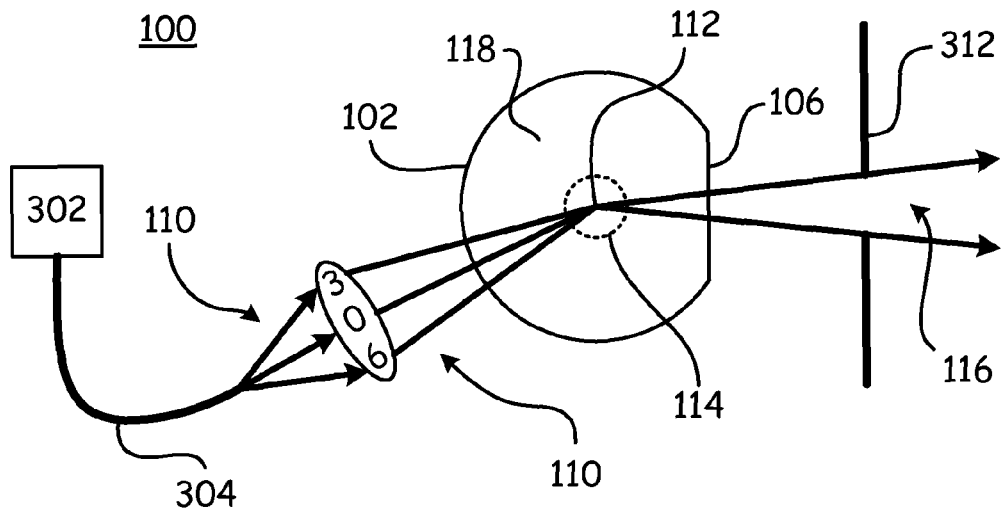
FIG. 5 is a cross-sectional view of a light source according to a third embodiment of the present invention.

FIG. 5 depicts a cross-sectional view of another embodiment of the present invention, where the cell 201 has a flat output window 106. In some embodiments the output window 106 is made of the same material as the cell 102. In other embodiments it is made of a different material. Because most of the cell 102 does not need to transmit vacuum ultraviolet wavelengths, the cell 102 in some embodiments is made of material that is not transmissive (or is poorly transmissive) at vacuum ultraviolet wavelengths, such as quartz or fused silica, or is made of a less pure grade of the same material as the window 106. In some embodiments the window 106 is made of a highly pure grade of sapphire and the rest of the cell 102 of a less pure grade of sapphire.

FIG. 8 depicts an embodiment where a single high-powered laser diode 302 focuses a beam 110 directly into the gas 118 to create the plasma 114. The laser diode 302 in one embodiment emits between about twenty watts and about two-hundred and fifty watts of infrared or visible radiation. The laser-diode light source 302 can be used in combination with any of the other features and embodiments described herein including, but not limited to, different configurations of lenses and minors for the focusing optics 306, anti-reflection coatings 308, and the cylinder 102, with or without flat windows 104 and 106.

Figure 9:
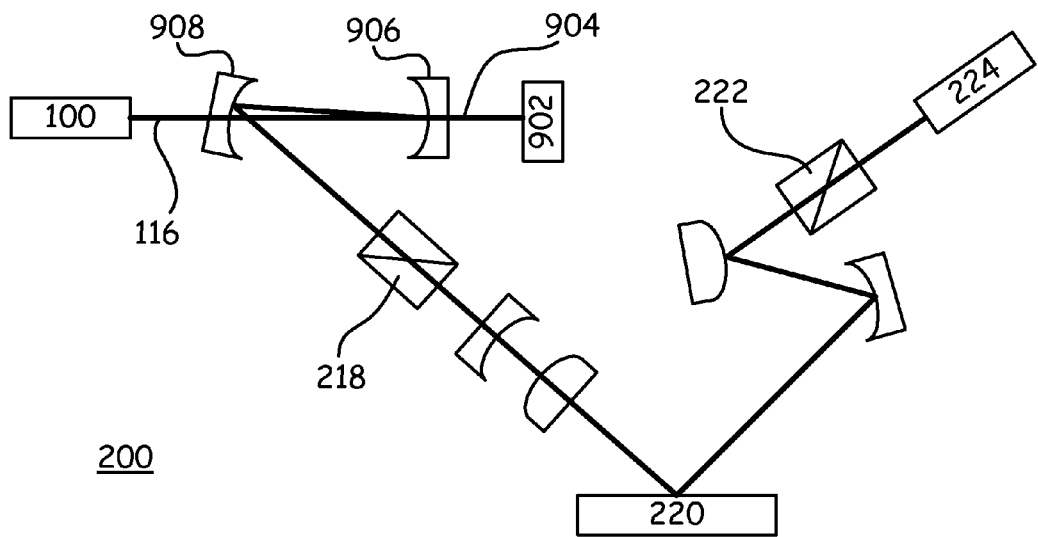
FIG. 9 is a functional block diagram of a broadband spectroscopic ellipsometer according to another embodiment of the present invention.

FIG. 9 depicts another embodiment of an ellipsometer 200. Again it should be understood that some of the optical elements depicted in FIGS. 9 and 10 may lie above or below the plane of the page and so are shown in projection. For example the light 116 passes in front of minor 908 and aperture 910 (both of which lie below the plane of the page in these figures) and is reflected off mirror 906. Mirror 906 is tilted at a slight angle so that the reflected light from 906 passes through aperture 910 and strikes minor 908. The light is reflected from 908 to polarizer 218. Other optical components may similarly lie above or below the plane of the page. This ellipsometer 200 includes a monitor 902 that monitors the intensity of the light 116 that is emitted from the light source 100. In this embodiment, the minor 906 reflects most of the light 116 that is incident upon it, but a small fraction 904 of the incident light 116 is transmitted to the monitor 902. The monitor 902 in some embodiments is a photodiode that monitors the intensity of the light source 100 over a wide range of wavelengths. In other embodiments it is a spectrometer that individually monitors the intensity of many wavelengths.

The signal from the monitor 902 in some embodiments is used to adjust the laser 302 within the light source 100 by, for example, controlling the current through a laser diode 302, to compensate for intensity fluctuations in the light source 100. In some embodiments the monitor 902 is part of a control loop that controls the light output 116 to be more stable than would be possible without the monitor 902. In an alternate embodiment, the signal from the monitor 902 is used to normalize the data collected by the spectrograph 224, and thereby to correct for fluctuations in the light source 100. This can be done wavelength by wavelength as described in U.S. Pat. No. 5,747,813, or by a single global correction value that is applied to all wavelengths.

Figure 10:
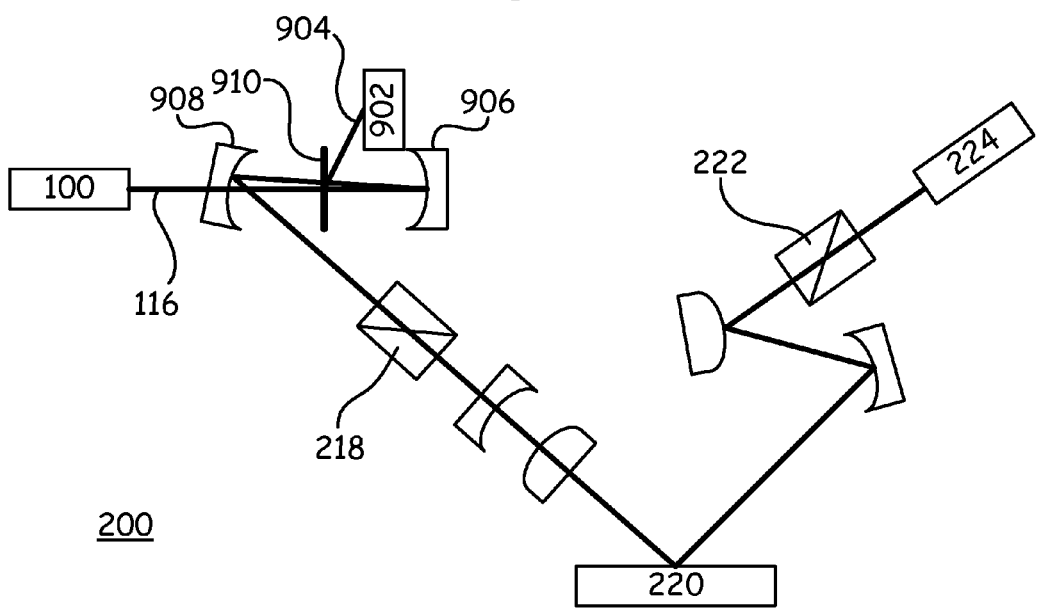
FIG. 10 is a functional block diagram of a broadband spectroscopic ellipsometer according to yet another embodiment of the present invention.

In various embodiments the monitor 902 is placed in different positions. For example, instead of mirror 906 transmitting a small fraction 904 of the incident radiation 116, the mirror 906 is opaque and the mirror 908 is partially transmissive, with the monitor 902 located behind the mirror 908. In yet another embodiment, aperture 910 is inclined at a slight angle to the main propagation direction of the light 116, and the monitor 902 is positioned so as to capture the light 904 that is reflected from the aperture 910 that is not transmitted through the aperture in 910, as depicted in FIG. 10.

In some embodiments, the polarizer 218 of the ellipsometer 200 incorporating the light source 100 is not rotated during data collection, but instead the analyzer 222 is rotated. In various embodiments, either or both of the analyzer 222 or polarizer 218 includes not just a polarizing element, but also a compensator (also known as a waveplate or retarder). In some embodiments, the compensator can be rotated instead of the polarizing element. In other embodiments, both the analyzer 222 and the polarizer 218 (or the compensators within those functions) are rotated, in some embodiments at different rotation speeds and in some embodiments in opposite directions.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A cell for a vacuum ultraviolet plasma light source, the cell comprising:
    a tube having cylindrical side walls and formed exclusively of sapphire,
    a first substantially flat end cap and a second substantially flat end cap diffusion bonded to opposing ends of the tube, the first and second end caps formed exclusively of sapphire, the end caps and the tube forming a closed cell,
    the first end cap disposed substantially perpendicular to the side walls of the tube, and the second end cap disposed oblique to the side walls of the tube,
    the second end cap coated with an anti-reflective coating so that the laser light directed into the cell through the coated second end cap exhibits a reduced degree of reflectance, and the first end cap not coated with the anti-reflective coating,
    the first end cap having a first purity grade of sapphire and the second end cap having a second purity grade of sapphire, where the first purity grade of sapphire is relatively greater than the second purity grade of sapphire,
    the second end cap for receiving a laser light along a second trajectory that is substantially perpendicular to the second end cap,
    the cell containing at least one noble gas that is ionizable to a plasma for producing an ultraviolet light, and
    the first end cap for expelling the ultraviolet light along a first trajectory that is substantially perpendicular to the first end cap, and askew to the second trajectory.

2. The cell of claim 1, wherein the at least one noble gas includes at least one of xenon and argon, xenon and krypton, and xenon and neon.

3. The cell of claim 1, wherein the at least one noble gas includes mercury.

4. The cell of claim 1, further comprising electrodes extending through the tube into the cell, the electrodes hard-sealed to the sapphire of the tube.

5. A vacuum ultraviolet plasma light source, comprising:
    a cell comprising,
        a tube having cylindrical side walls and formed exclusively of sapphire,
        a first substantially flat end cap and a second substantially flat end cap diffusion bonded to opposing ends of the tube, the first and second end caps formed exclusively of sapphire, the end caps and the tube forming a closed cell,
        the first end cap disposed substantially perpendicular to the side walls of the tube, and the second end cap disposed oblique to the side walls of the tube,
        the second end cap coated with an anti-reflective coating so that the laser light directed into the cell through the coated second end cap exhibits a reduced degree of reflectance, and the first end cap not coated with the anti-reflective coating,
        the first end cap having a first purity grade of sapphire and the second end cap having a second purity grade of sapphire, where the first purity grade of sapphire is relatively greater than the second purity grade of sapphire,
        the second end cap for receiving a laser light along a second trajectory that is substantially perpendicular to the second end cap,
        the cell containing at least one noble gas that is ionizable to a plasma for producing an ultraviolet light, and
        the first end cap for expelling the ultraviolet light along a first trajectory that is substantially perpendicular to the first end cap, and askew to the second trajectory,
    means for initiating the plasma within the cell, and
    means for sustaining the plasma within the cell.

6. The vacuum ultraviolet plasma light source of claim 5, wherein the means for initiating the plasma within the cell includes at least one of a direct current potential applied by electrodes extending into the cell, an alternating current potential applied by electrodes extending into the cell, a pulsed laser light directed into the cell, a continuous laser light directed into the cell, microwaves directed into the cell, radio frequency electromagnetic radiation directed into the cell, ionizing radiation of gamma rays directed into the cell, ionizing radiation of X-rays directed into the cell, ionizing radiation of alpha particles directed into the cell, and ionizing radiation of beta particles directed into the cell.

7. The vacuum ultraviolet plasma light source of claim 5, wherein the means for sustaining the plasma within the cell includes at least one of a direct current potential applied by electrodes extending into the cell, an alternating current potential applied by electrodes extending into the cell, a pulsed laser light directed into the cell, and a continuous laser light directed into the cell.

8. The vacuum ultraviolet plasma light source of claim 5, wherein the means for sustaining the plasma comprises a laser light source coupled to a fiber optic for directing the laser light into the cell.

9. A spectrographic instrument, comprising:
   a vacuum ultraviolet plasma light source, comprising,
      a cell comprising,
         a tube having cylindrical side walls and formed exclusively of sapphire,
         a first substantially flat end cap and a second substantially flat end cap diffusion bonded to opposing ends of the tube, the first and second end caps formed exclusively of sapphire, the end caps and the tube forming a closed cell,
         the first end cap disposed substantially perpendicular to the side walls of the tube, and the second end cap disposed oblique to the side walls of the tube,
         the second end cap coated with an anti-reflective coating so that the laser light directed into the cell through the coated second end cap exhibits a reduced degree of reflectance, and the first end cap not coated with the anti-reflective coating,
         the first end cap having a first purity grade of sapphire and the second end cap having a second purity grade of sapphire, where the first purity grade of sapphire is relatively greater than the second purity grade of sapphire,
         the second end cap for receiving a laser light along a second trajectory that is substantially perpendicular to the second end cap,
         the cell containing at least one noble gas that is ionizable to a plasma for producing a vacuum ultraviolet light, and
         the first end cap for expelling the ultraviolet light along a first trajectory that is substantially perpendicular to the first end cap, and askew to the second trajectory,
      means for initiating the plasma within the cell, and
      means for sustaining the plasma within the cell,
   a polarizer for imparting a desired polarization to the vacuum ultraviolet light,
   optical elements for directing the polarized vacuum ultraviolet light to impinge upon and reflect from a substrate,
   optical elements for receiving the reflected polarized vacuum ultraviolet light from the substrate,
   an analyzer for filtering portions of the reflected polarized vacuum ultraviolet light, and
   a spectrometer for creating signals associated with the filtered reflected polarized vacuum ultraviolet light.

10. The spectrographic instrument of claim 9, wherein:
the means for initiating the plasma within the cell includes at least one of a direct current potential applied by electrodes extending into the cell, an alternating current potential applied by electrodes extending into the cell, a pulsed laser light directed into the cell, a continuous laser light directed into the cell, microwaves directed into the cell, radio frequency electromagnetic radiation directed into the cell, ionizing radiation of gamma rays directed into the cell, ionizing radiation of X-rays directed into the cell, ionizing radiation of alpha particles directed into the cell, and ionizing radiation of beta particles directed into the cell, and
the means for sustaining the plasma within the cell includes at least one of a direct current potential applied by electrodes extending into the cell, an alternating current potential applied by electrodes extending into the cell, a pulsed laser light directed into the cell, and a continuous laser light directed into the cell.

* * * * *